(12) United States Patent
Lurie et al.

(10) Patent No.: US 7,174,891 B2
(45) Date of Patent: Feb. 13, 2007

(54) CPR MASK WITH COMPRESSION TIMING METRONOME AND METHODS

(75) Inventors: Keith G. Lurie, Minneapolis, MN (US); Gene Scharenbroich, Newport, MN (US); Todd M. Zielinski, Minneapolis, MN (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 642 days.

(21) Appl. No.: 10/396,007

(22) Filed: Mar. 24, 2003

(65) Prior Publication Data

US 2003/0192547 A1 Oct. 16, 2003

Related U.S. Application Data

(63) Continuation of application No. 09/532,601, filed on Mar. 22, 2000, now abandoned, and a continuation-in-part of application No. 10/224,263, filed on Aug. 19, 2002, now Pat. No. 6,986,349, which is a continuation-in-part of application No. 10/119,203, filed on Apr. 8, 2002, which is a continuation-in-part of application No. 09/854,238, filed on May 11, 2001, now Pat. No. 6,604,523, which is a continuation-in-part of application No. 09/546,252, filed on Apr. 10, 2000, now Pat. No. 6,526,973, which is a continuation of application No. 08/950,702, filed on Oct. 15, 1997, now Pat. No. 6,062,219, which is a continuation-in-part of application No. 08/403,009, filed on Mar. 10, 1995, now Pat. No. 5,692,498, which is a continuation-in-part of application No. 08/149,203, filed on Nov. 9, 1993, now Pat. No. 5,441,658.

(51) Int. Cl.
*A61M 16/00* (2006.01)
*A62B 18/02* (2006.01)
*G09B 15/00* (2006.01)
*A61N 1/372* (2006.01)

(52) U.S. Cl. ............................ 128/204.23; 128/205.25; 128/206.21; 128/207.16; 84/484; 607/15; 607/42

(58) Field of Classification Search .................... None
See application file for complete search history.

(56) References Cited

U.S. PATENT DOCUMENTS 1,848,232 A * 3/1932 Swope et al. .......... 128/205.23

(Continued)

FOREIGN PATENT DOCUMENTS

CA 668771 8/1963

(Continued)

OTHER PUBLICATIONS

"Guidelines for Cardiopulmonary Resuscitation and Emergency Cardiac Care," JAMA, 1992; 268; 2172-2295.

(Continued)

*Primary Examiner*—Glenn K. Dawson
(74) *Attorney, Agent, or Firm*—Townsend and Townsend and Crew LLP

(57) ABSTRACT

A facial mask includes a mask body that is adapted to be coupled to a patient's face. A valve system is coupled to the mask body to permit the inflow of respiratory gasses into the mask body and to permit the outflow of respiratory gasses from the mask body. A metronome is coupled to the mask body to produce a repeating chest compression signal to facilitate the performance of regular chest compressions when performing cardio pulmonary resuscitation. The metronome may also produce a ventilation signal to facilitate the proper ventilation of the patient.

34 Claims, 8 Drawing Sheets

U.S. PATENT DOCUMENTS

| | | | |
|---|---|---|---|
| 2,774,346 A | | 12/1956 | Halliburton |
| 3,191,596 A | | 6/1965 | Bird et al. |
| 3,307,541 A | | 3/1967 | Hewson |
| 3,357,426 A | * | 12/1967 | Cohen .................. 128/202.27 |
| 3,662,751 A | | 5/1972 | Barkalow et al. |
| 3,669,108 A | | 6/1972 | Sundblom et al. |
| 3,794,043 A | | 2/1974 | McGinnis |
| 3,815,606 A | | 6/1974 | Mazal |
| 3,834,383 A | | 9/1974 | Weigl et al. |
| 3,933,171 A | | 1/1976 | Hay |
| 4,041,943 A | | 8/1977 | Miller |
| 4,077,400 A | | 3/1978 | Harrigan |
| 4,077,404 A | | 3/1978 | Elam |
| 4,095,590 A | | 6/1978 | Harrigan |
| 4,166,458 A | | 9/1979 | Harrigan |
| 4,226,233 A | | 10/1980 | Kritzer |
| 4,237,872 A | * | 12/1980 | Harrigan ..................... 601/1 |
| 4,259,951 A | | 4/1981 | Chernack et al. |
| 4,297,999 A | * | 11/1981 | Kitrell .................. 128/205.16 |
| 4,298,023 A | | 11/1981 | McGinnis |
| 4,316,458 A | | 2/1982 | Hammerton-Fraser |
| 4,320,754 A | | 3/1982 | Watson et al. |
| 4,397,306 A | | 8/1983 | Weisfeldt et al. |
| 4,446,864 A | | 5/1984 | Watson et al. |
| 4,449,526 A | | 5/1984 | Elam |
| 4,481,938 A | | 11/1984 | Lindley |
| 4,533,137 A | | 8/1985 | Sonne |
| 4,588,383 A | | 5/1986 | Parker et al. |
| 4,598,706 A | * | 7/1986 | Darowski et al. ...... 128/205.24 |
| 4,601,465 A | | 7/1986 | Roy |
| 4,881,527 A | | 11/1989 | Lerman |
| 4,898,166 A | | 2/1990 | Rose et al. |
| 4,971,051 A | | 11/1990 | Toffolon |
| 5,042,500 A | * | 8/1991 | Norlien et al. ............... 600/532 |
| 5,050,593 A | | 9/1991 | Poon |
| 5,056,505 A | | 10/1991 | Warwick et al. |
| 5,109,840 A | | 5/1992 | Daleiden |
| 5,163,424 A | | 11/1992 | Kohnke |
| 5,193,544 A | | 3/1993 | Jaffe |
| 5,217,006 A | | 6/1993 | McCulloch |
| 5,235,970 A | | 8/1993 | Augustine |
| 5,239,988 A | * | 8/1993 | Swanson et al. ............... 601/41 |
| 5,295,481 A | | 3/1994 | Geeham |
| 5,301,667 A | | 4/1994 | McGrail et al. |
| 5,305,743 A | | 4/1994 | Brain |
| 5,355,879 A | | 10/1994 | Brain |
| 5,359,998 A | | 11/1994 | Lloyd |
| 5,392,774 A | | 2/1995 | Sato |
| 5,454,779 A | | 10/1995 | Lurie et al. |
| 5,551,420 A | * | 9/1996 | Lurie et al. ............. 128/205.13 |
| 5,588,422 A | * | 12/1996 | Lurie et al. ............. 128/200.24 |
| 5,628,305 A | | 5/1997 | Melker |
| 5,645,522 A | | 7/1997 | Lurie et al. |
| 5,657,751 A | * | 8/1997 | Karr, Jr. ................. 128/205.18 |
| 5,692,498 A | * | 12/1997 | Lurie et al. ............. 128/205.24 |
| 5,704,346 A | | 1/1998 | Inoue |
| 5,730,122 A | * | 3/1998 | Lurie .................... 128/207.12 |
| 6,010,470 A | | 1/2000 | Albery et al. |
| 6,029,667 A | | 2/2000 | Lurie |
| 6,062,219 A | * | 5/2000 | Lurie et al. ............. 128/205.24 |
| 6,155,257 A | | 12/2000 | Lurie et al. |
| 6,165,105 A | | 12/2000 | Boutellier et al. |
| 6,174,295 B1 | * | 1/2001 | Cantrell et al. ................ 601/41 |
| 6,224,562 B1 | | 5/2001 | Lurie et al. |
| 6,234,985 B1 | | 5/2001 | Lurie et al. |
| 6,312,399 B1 | | 11/2001 | Lurie et al. |
| 6,356,785 B1 | * | 3/2002 | Snyder et al. .................. 607/5 |
| 6,425,393 B1 | | 7/2002 | Lurie et al. |
| 6,459,933 B1 | | 10/2002 | Lurie et al. |
| 6,483,327 B1 | | 11/2002 | Lurie et al. |
| 6,526,973 B1 | | 3/2003 | Lurie et al. |
| 6,587,726 B2 | | 7/2003 | Lurie et al. |
| 2002/0069878 A1 | | 6/2002 | Lurie et al. |
| 2002/0170562 A1 | | 11/2002 | Lurie et al. |
| 2003/0037784 A1 | | 2/2003 | Lurie |
| 2003/0062041 A1 | | 4/2003 | Lurie et al. |

FOREIGN PATENT DOCUMENTS

| | | |
|---|---|---|
| CA | 2 077 608 | 3/1993 |
| DE | 24 53 490 | 5/1975 |
| EP | 0 029 352 A1 | 5/1981 |
| EP | 0 139 363 A1 | 5/1985 |
| EP | 0 245 142 A1 | 11/1987 |
| EP | 0 367 285 B1 | 5/1990 |
| EP | 0 411 714 A1 | 10/1992 |
| EP | 0 509 773 A1 | 10/1992 |
| GB | 1 465 127 | 2/1977 |
| GB | 2 139 099 | 11/1984 |
| WO | WO90/05518 | 5/1990 |
| WO | WO93/21982 | 11/1993 |
| WO | WO95/13108 | 5/1995 |
| WO | WO95/28193 | 10/1995 |
| WO | WO96/28215 | 9/1996 |

OTHER PUBLICATIONS

"Ventilators—Theory and Clinical Application," Dupuis, C.V. Mosby Co., St. Louis, MO @ 1986, pp. 447-448, 481,496, ISBN 081614201.

Directions for use Ambu® CardioPump™, pp. 1-8.

Cohen et al. (1992) "Active compression-decompression resuscitation: A novel method of cardiopulmonary resuscitation," *American Heart Journal* 124 (5):1145-1150.

Cohen et al. (1992) "Active Compression-Decompression A New Method of Cardiopulmonary Resuscitation." *JAMA* 267 (21):2916-2923.

Lindner et al (1993) "Effects of Active Compression-Decompression Resuscitation on Myocardial and Cerebral Resuscitation Blood Flow in Pigs." *Circulation* 88 (3):1254-1263.

Lurie et al. (1995) "Regulated to Death: The Matter of Informed Consent for Human Experimentation in Emergency Resuscitation Research." *PACE* 18:1443-1447.

Mushin W.W. et al., "Automatic Ventilation of the Lungs—The Lewis-Leigh Inflating Valve," *Blackwell Scientific*, Oxford, GB, p. 838.

* cited by examiner

CPR MASK WITH COMPRESSION TIMING METRONOME AND METHODS

This application is a continuation application of U.S. patent application Ser. No. 09/532,601, filed Mar. 22, 2000 now abandoned. This application is also a continuation in part application of U.S. patent application Ser. No. 10/224,263, filed Aug. 19, 2002 now U.S. Pat. No. 6,986,349, which is a continuation in part application of U.S. patent application Ser. No. 10/119,203, filed Apr. 8, 2002, which is a continuation in part application of U.S. patent application Ser. No. 09/854,238, filed May 11, 2001 now U.S. Pat. No. 6,604,523, which is a continuation in part application of U.S. patent application Ser. No. 09/546,252, filed Apr. 10, 2000 now U.S. Pat. No. 6,526,973, which is a continuation of U.S. patent application Ser. No. 08/950,702, filed Oct. 15, 1997 (now U.S. Pat. No. 6,062,219), which is a continuation-in-part application of U.S. patent application Ser. No. 08/403,009, filed Mar. 10, 1995 (now U.S. Pat. No. 5,692,498), which is a continuation-in-part application of U.S. patent application Ser. No. 08/149,204, filed Nov. 9, 1993 (now U.S. Pat. No. 5,551,420), the disclosures of which are herein incorporated by reference.

BACKGROUND OF THE INVENTION

This invention relates generally to the field of resuscitation, and in particular, to the field of cardiopulmonary resuscitation. More specifically, the invention is related to techniques for assisting a rescuer in performing appropriately timed chest compressions and in ventilating a patient.

Sudden cardiac arrest is a significant cause of death throughout the world. The performance of cardiopulmonary resuscitation (CPR) is one well-accepted technique to assist in restoring cardiac function. The effectiveness of CPR may depend upon the manner of its performance. For example, when performing CPR it may be desirable to compress the chest at a certain rate. Also, it may be desirable to perform chest compressions according to a certain rhythm as described generally in "The Guidelines of for CPR and Emergency Cardiovascular Care", JAMA, 1992; 268: 2172–2295, the complete disclosure of which is herein incorporated by reference. Even when properly trained, however, the correct performance of CPR on a patient can be difficult. For example, it may be difficult to evaluate whether chest compressions are being performed at an optimal rate.

When performing CPR, it may also be desirable to periodically ventilate the patient, e.g., using mouth to mouth resuscitation. However, the proper timing of ventilations may be difficult to evaluate when performing CPR. Further, many ventilation techniques may transfer respiratory pathogens between the rescuer and the patient.

Hence, the invention is related to techniques for facilitating the performance of CPR, and in particular, to the manner in which chest compressions and/or ventilations are performed. The invention is also related to techniques for preventing the transfer of contaminants between the rescuer and patient when providing ventilation.

SUMMARY OF THE INVENTION

The invention provides exemplary facial masks that may be used when performing cardiopulmonary resuscitation (CPR). In one embodiment, a facial mask comprises a mask body that is adapted to be coupled to a patient's face. The mask also includes a valve system to permit the inflow of respiratory gases into the mask body and to permit the outflow of respiratory gases from the mask body. A metronome is coupled to the mask body to produce a repeating audio and/or visual signal upon its actuation. In turn, the repeating signal may be used to facilitate the performance of regular chest compressions when performing CPR. By including the metronome with the mask body, a rescuer is provided with the ability to facilitate the proper performance of CPR without requiring extra peripheral equipment.

In one aspect, the metronome may be configured to produce the repeating audio and/or visual signal at a constant rate in the range from about 50 signals per minute to about 100 signals per minute. Optionally, the metronome may include a light source and/or a speaker to produce a flashing light or an audible tone or voice command to indicate when chest compressions should be performed.

In another particular aspect, the metronome may be configured to produce a chest compression signal and a ventilation signal. In this way, the rescuer may perform chest compressions in cadence with the chest compression signal and perform ventilations in cadence with the ventilation signal. For example, the chest compression signal may be a flashing light, while the ventilation signal may comprise an audible sound, or vice versa. As another example, the signals may be differentiated by different colored flashing lights or different audible tones. In another aspect, the ventilation signal may be produced one to two times about every 5 to about 25 chest compression signals.

In another particular aspect, the valve system may be provided with an inhalation port and an exhalation port. Conveniently, the valve system may be configured such that respiratory gases are permitted to flow through the inhalation port when respiratory gases are introduced into the mask through the inhalation port. Further, expired gases are permitted to flow out of the exhalation port while being prevented from passing through the inhalation port. In one aspect, the valve system may include a fish mouth membrane valve unit that is configured to block gas flow to the exhalation port when gases are introduced into the inhalation port. The valve unit is also configured to permit gases expired from the patient to flow to the exhalation port while preventing the gases from flowing to the inhalation port. Conveniently, a filter may be disposed across the inhalation port to prevent contaminants from passing from the rescuer to the patient.

In one particular aspect, the valve system may further include an inspiratory impedance threshold valve that is constructed similar to those described in U.S. Pat. Nos. 5,551,420 and 5,692,498, the complete disclosures of which are herein incorporated by reference. In this way, inspiratory gases are prevented from entering into the mask until a threshold negative intrathoracic pressure within the patient is met or exceeded. The valve system may further include a positive end expiration valve similar to those described in U.S. Pat. Nos. 5,551,420 and 5,692,498 to prevent gases from escaping from the mask until a certain pressure within the mask is met or exceeded.

In another aspect, an inflatable bladder may be coupled to the bottom end of the mask to assist in providing a seal between the patient's face and mask body. In another aspect, a power supply may be coupled to the mask body, or incorporated within the mask body, to supply power to the metronome. In still another aspect, one or more straps may be coupled to the mask body to facilitate coupling of the mask to the patient's face. An adhesive may be used alone or in combination with the straps and/or inflatable bladder to facilitate coupling of the mask to the patient's face. In still another aspect, a mouthpiece may be attached to the facial mask to facilitate the performance of mouth to mask ventilation.

The invention further provides an exemplary method for performing CPR. According to the method, a mask is coupled to the patient's face, with the mask having a metronome and a valve system to permit the inflow of respiratory gases into the mask and to permit the outflow of respiratory gases from the mask. The metronome is actuated to produce a repeating signal, and chest compressions are performed in cadence with the repeating signal. Hence, with such a method, a facial mask may easily be coupled to the patient's face and the metronome actuated to produce a repeating signal that is employed to facilitate the proper performance of CPR.

In one particular aspect, respiratory gases may be prevented from flowing into the mask until a threshold negative pressure is met or exceeded. In this way, CPR efficiency may be increased, with proper performance of CPR being facilitated by the signals produced from the metronome. Also, expired respiratory gases may be prevented from exiting the mask until a certain pressure within the mask is met or exceeded.

In one aspect, the repeating signal is produced at a constant rate in the range from about 50 signals per minute to about 100 signals per minute. Conveniently, the metronome may produce a flashing light or an audible tone when each chest compression is to be performed.

In another aspect, a respiratory gas is periodically supplied through the valve system. This may be accomplished, for example, by having the rescuer blow into the inhalation port, by coupling a ventilatory bag to the inhalation port and squeezing the bag, and the like. In one particular aspect, the valve system may be employed to prevent any expired respiratory gases from the patient from passing through the inhalation port. The valve system may further be configured to permit any expired respiratory gases to exit the exhalation port following ventilation. In this way, expired respiratory gases from the patient are prevented from reaching the rescuer. Conveniently, the respiratory gases from the rescuer to the patient may be filtered to prevent respiratorial contaminants from reaching the patient.

Conveniently, the mask may include an on/off switch to permit the rescuer to operate the switch and begin the metronome when ready to perform CPR. In addition, the metronome and an accompany power supply (such as batteries) may be detached from the mask to facilitate cleaning of the mask and charging and/or replacement of the batteries. Conveniently, straps may be provided to permit the rescuer to strap the facial mask to the patient's face. An adhesive may also be used to couple the mask to the patient's face.

In still another embodiment, the invention provides a kit that may be used when performing CPR. The kit includes a facial mask having a valve system to permit respiratory gases to be supplied to the patient through the mask. A carrying case is also provided to provide a convenient way to carry the mask. For example, the carrying case may comprise a housing for holding the mask. The carrying case includes a metronome that may be actuated by the rescuer when performing CPR. A mouthpiece connector may also be provided to facilitate mouth to mask ventilation. Further, an impedance threshold valve and/or a positive end expiration valve may also be provided to regulate gas inflow and outflow as previously described. These valves may be incorporated into the mask or may be configured to be detachable.

Hence, with such a kit, the rescuer simply needs to remove the mask from the carrying case and place it on the patient's face. The metronome of the carrying case may then be actuated to assist the rescuer in performing regular chest compressions when performing CPR. Conveniently, the carrying case may include a strap, a belt, or the like to permit the carrying case to be secured to the rescuer. In this way, the mask and metronome may easily be carried with the rescuer.

The facial masks of the invention may be used when performing a wide variety of procedures. These may include, for example, manual closed chest CPR, ACD CPR, interposed abdominal counterpulsation CPR, CPR with a life stick or a vest, open chest CPR techniques, techniques utilizing minimally invasive cardiac compression devices, CPR with devices which increase and/or decrease intrathoracic pressures, and the like.

In another embodiment, electrodes may be coiled inside of the mask in the resting state and extended outward to the neck region of the patient when the mask is employed. The stimulation electrodes may be controlled and power may be supplied by an electrical control system. The facial mask metronome may be coupled to the control system so that manual chest stimulation and phrenic nerve stimulation may be synchronously performed using the metronome.

DESCRIPTION OF THE SPECIFIC EMBODIMENTS

Figure 1:
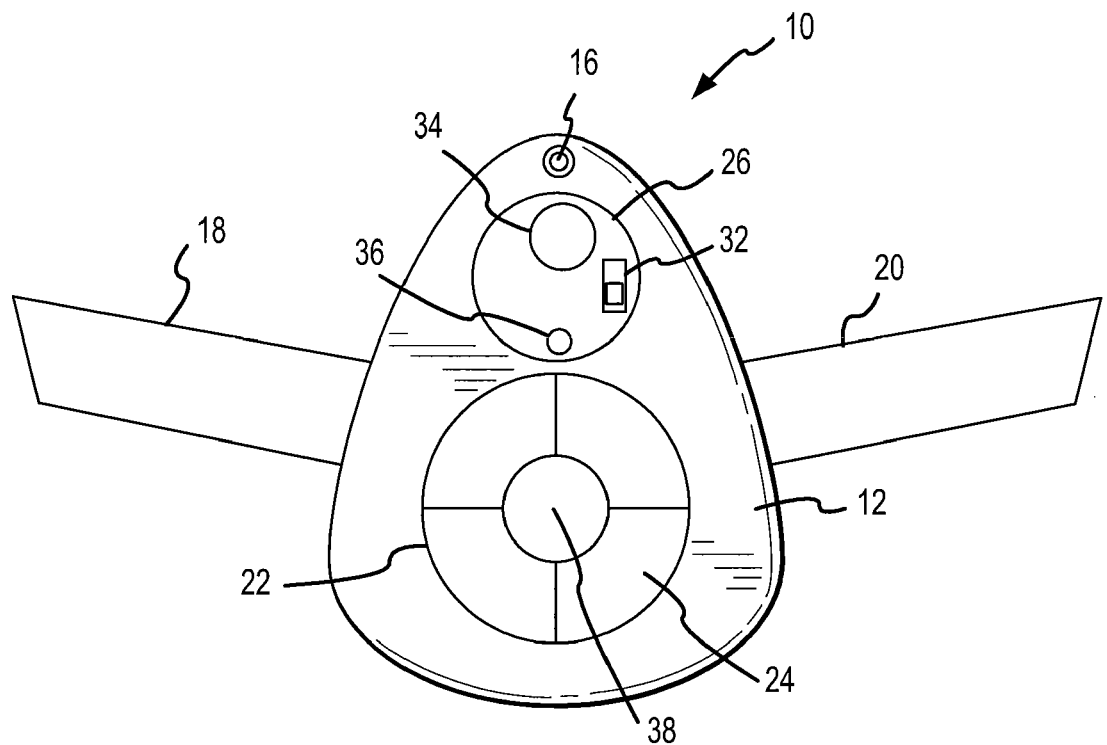
FIG. 1 is a top view of one embodiment of a facial mask having a metronome according to the invention.

In one embodiment, the invention provides a facial mask that incorporates a metronome to assist a rescuer in the performance of CPR. The facial mask is configured to be secured to a patient's face to facilitate ventilation of the patient while performing CPR. The mask may be secured manually by the rescuer, by use of an adhesive, or by the use of straps placed around the patient's head. By incorporating a metronome, a chest compression signal may be produced to guide the rescuer in performing regular and appropriately timed chest compressions. For example, the metronome may produce a repeating chest compression signal that repeats at a constant rate in the range from about 50 signals per minute to about 100 signals per minute, and more preferably at about 80 signals per minute. The metronome may also be configured to produce a regular and repeating ventilation signal to indicate when the patient should be ventilated. For example, the ventilation signal may be produced one to two times about every 5 to 25 chest compression signals to indicate that a ventilation should be performed.

A variety of signals may be employed to indicate when chest compressions or ventilations should be performed. Such signals may include, for example, visual signals, audible signals, and the like. Merely by way of example, such signals may include a flashing light, a beep, a voice, a whistle, a bell, vibrations, and the like. Different types of the same signal or different signals may be used to differentiate between a chest compression signal and a ventilation signal. For example, the signals may be differentiated based on colors, sound levels, frequency, pitch, voice commands, and the like, as well as the use of different types of signals. Merely by way of example, an audible beep may be produced each time a chest compression is to be performed while an audible "breathe" would be produced to indicate that a ventilation should be performed. Hence, such a cadence would be as follows: "beep, beep, beep, beep, breathe, beep . . . " Further, it will be appreciated that different types of signals may be produced at the same time to enhance their perception. For example, a flashing light and a beep may be produced at the same time to indicate that a chest compression should occur.

The facial masks may also utilize a valve system to permit the exchange of respiratory gases. The facial masks and/or valve systems may have a variety of designs, and may be constructed of a variety of materials, including rubber, silicone, plastic, polyurethane, polycarbonate, acrylic, blends, other synthetic poly carbons, and the like. In one aspect, the valve system may be configured to prevent respiratory gases or fluids produced by the patient from coming into contact with the rescuer. For example, the valve system may include an inhalation port that is only opened during ventilation so that gases from the patient are not able to exit through the inhalation port. Further, the valve system may include an exhalation port that is apart from the inhalation port to permit the exit of respiratory gases from the patient only through the exit port. Preferably, the exit of respiratory gases from the patient will be permitted only after a ventilation has stopped.

In one particular embodiment, a face mask system may include a facial mask that is coupled to an inspiratory impedance valve as described in U.S. Pat. Nos. 5,551,420 and 5,692,498. The system may further include a mouthpiece, a detachable metronome, and an expiratory port that is spaced apart from the inspiratory port.

In another embodiment, the invention provides a kit that may be used when performing CPR. The kit includes a carrying case that incorporates a metronome that may be similar to the other metronomes described herein. The carrying case is utilized to carry a facial mask that has a valve system to permit the exchange of respiratory gases. In this way, a rescuer may conveniently carry the carrying case to a location where the patient is to be treated. The mask may then be removed from the case and coupled to the patient's face. The metronome in the carrying case is then actuated to facilitate the performance of CPR in a manner similar to that previously described. The kit may further include a power source, stimulating electrodes, an impedance threshold valve and a mouthpiece for mouth to mask ventilation.

Figure 2:
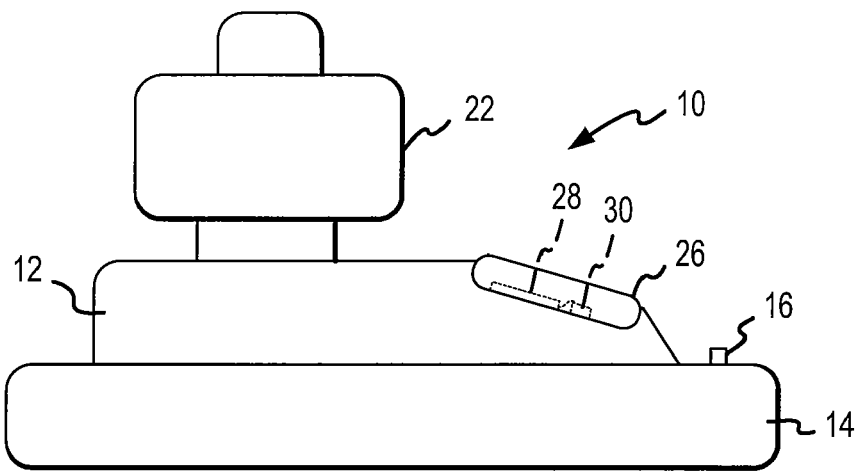
FIG. 2 is a side view of the facial mask of FIG. 1.

Referring now to FIGS. 1 and 2, one embodiment of a facial mask 10 will be described. Mask 10 comprises a mask body 12 to which is coupled an inflatable bladder 14 (see FIG. 2) or other flexible surface capable of maintaining an airtight seal between the mask and the face. An optional inflation port 16 is provided to facilitate inflation of bladder 14. When bladder 14 is inflated and pressed against the patient's face, a seal is provided with the patient's face to prevent the escape of respiratory gases from the interface between the mask and the patient's face.

Conveniently, a pair of head straps 18 and 20 are provided to facilitate the attachment of mask 10 to the patient's face. Conveniently, straps 18 and 20 may include a hook and loop fastener material, such as a Velcro™ material to facilitate convenient coupling of the two straps. When properly attached to the patient's face, mask body 12 covers the patient's mouth and nose so that a supply of respiratory gases into mask body 12 will be transferred to the patient's airway.

Facial mask 10 further includes a housing 22 for housing a valve system 24 (see also FIGS. 3 and 4) and a metronome module 26. As best shown in FIG. 2, metronome module 26 comprises a metronome circuit 28 that is configured to produce one or more repeating electrical signals that in turn are employed to produce repeating chest compression signals and ventilation signals as described in greater detail hereinafter. A battery 30 is also included to supply power to metronome circuit 28. Conveniently, battery 30 may comprise a low-voltage battery, such as a 0.2 to 6 volt D.C. battery. An on/off slide switch 32 is provided to turn metronome module 26 on and off.

Electrically coupled to metronome circuit 28 is an audio speaker 34 that is configured to produce a repeating audible signal as dictated by metronome circuit 28. Audio speaker 34 may be configured to produce a wide variety of sounds, such as speech, beeps, and the like. A light source 36, such as a light emitting diode (LED), may be coupled to circuit 28 to provide visual signals to assist in the performance of CRP. Alternatively, multiple LEDs that are covered by a translucent ring (not shown) may optionally be electrically coupled to metronome circuit 28. In this way, a repeating visual signal may be produced to indicate that a chest compression or ventilation should be performed. Optionally, the translucent ring may be divided into separate sections having different colors, and metronome circuit 28 may be configured to light selective LEDs to produce different colors. This may be used, for example, to separately indicate when a chest compression or a ventilation should be performed. As another alternative, metronome circuit 28 may be configured to illuminate various LEDs at different intensities to differentiate between a chest compression signal and ventilation signal. Optionally, the audible signals and visual signals may be produced simultaneously to apprise the rescuer that it is time to perform a chest compression or ventilation. Alternatively, the audible signal may be used to indicate a chest compression while a visual signal is used to indicate that a ventilation should be performed, or vice versa.

Module 26 may be configured to be detachable from mask body 12. In this way, mask body 12 may be cleaned without damaging the components of module 26. Further, module 26 may be removed and disassembled to replace or recharge battery 30.

Figure 3:
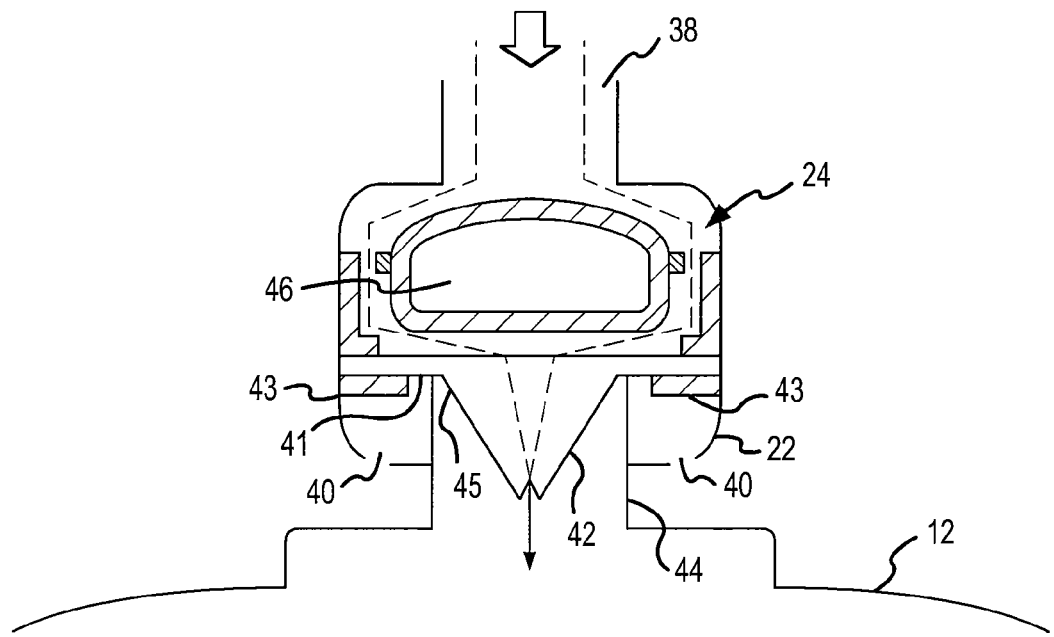
FIG. 3 is a partial cutaway side view of the mask of FIG. 2 when respiratory gases are being supplied to the patient.
Figure 4:
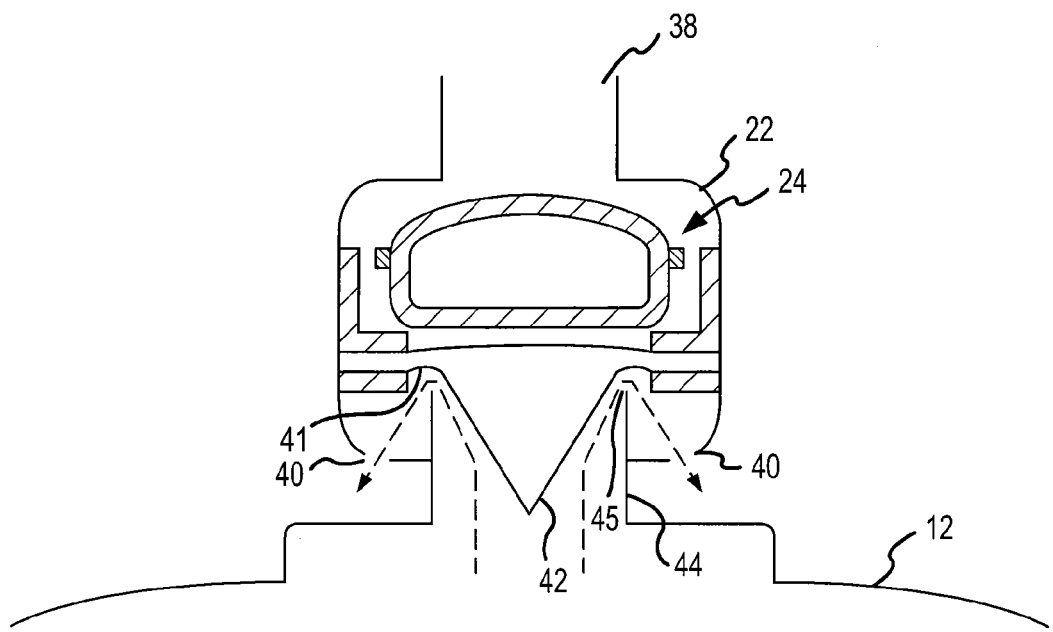
FIG. 4 illustrates the mask of FIG. 3 when the patient exhales.

Referring primarily now to FIGS. 3 and 4, construction of valve system 24 will be described. In so doing, it will be appreciated that mask 10 may include other types of valve systems and that the invention is not intended to be limited to the specific valve system illustrated in FIGS. 3 and 4. Valve system 26 comprises an inhalation port 38 through which respiratory gasses that are to be supplied to the patient may be directed. Conveniently, inhalation port 38 may be configured to receive respiratory gasses directly from a rescuer that blows respiratory gasses through inhalation port 38. Optionally, a mouthpiece may be coupled to port 38 to assist with ventilations. Alternatively, a compressible bag may be coupled to inhalation port 38 so that respiratory gasses may be supplied through inhalation port 38 when the bag is squeezed. As described hereinafter, an impedance threshold valve may be coupled to port 38 to further regulate gas flow. When such a valve is used, its inhalation port effectively becomes the inhalation port for valve system 26.

System 24 further includes an exhalation port 40 through which gasses expired by the patient are directed and exhausted from mask body 12. A membrane 41 having an integral fish mouth valve 42 is placed across housing 22 and is supported by a membrane support 43. System 24 further includes a tubular member 44 that couples system 24 to mask body 12. Membrane 41 is positioned over a top end 45 of tubular member 44. Conveniently, an airflow deflector 46 is positioned between port 38 and membrane 41.

When ventilating the patient, respiratory gases are forced through inhalation port 38 as shown by the arrow. These gases are deflected by deflector 46 and pass through fish mouth valve 42 as shown in FIG. 3. As the gases flow against membrane 41, a seal is provided between top end 45 and membrane 41 to prevent the gases from escaping through port 40. Optionally, valve system 24 may include a filter (not shown) that is disposed across inhalation port 38. In this way, respiratory gases which are introduced into inhalation port 38 are filtered before reaching the patient.

When the patient exhales (or gases are forced from the patient), the pressure generated from the expired gases causes fish mouth valve 42 to close, directing the expired gases to flow through tubular member 44 and cause membrane 41 to lift off of top end 45. In this way, the expired gasses will be forced out through exhalation port 40 and away from the rescuer to prevent any contaminants from reaching the rescuer as shown in FIG. 4. Optionally, a positive threshold valve may be placed across port 40 to prevent the gases from escaping until a certain positive intrathoracic pressure is met or exceeded as described generally in U.S. Pat. Nos. 5,551,420 and 5,692,498.

Figure 5:
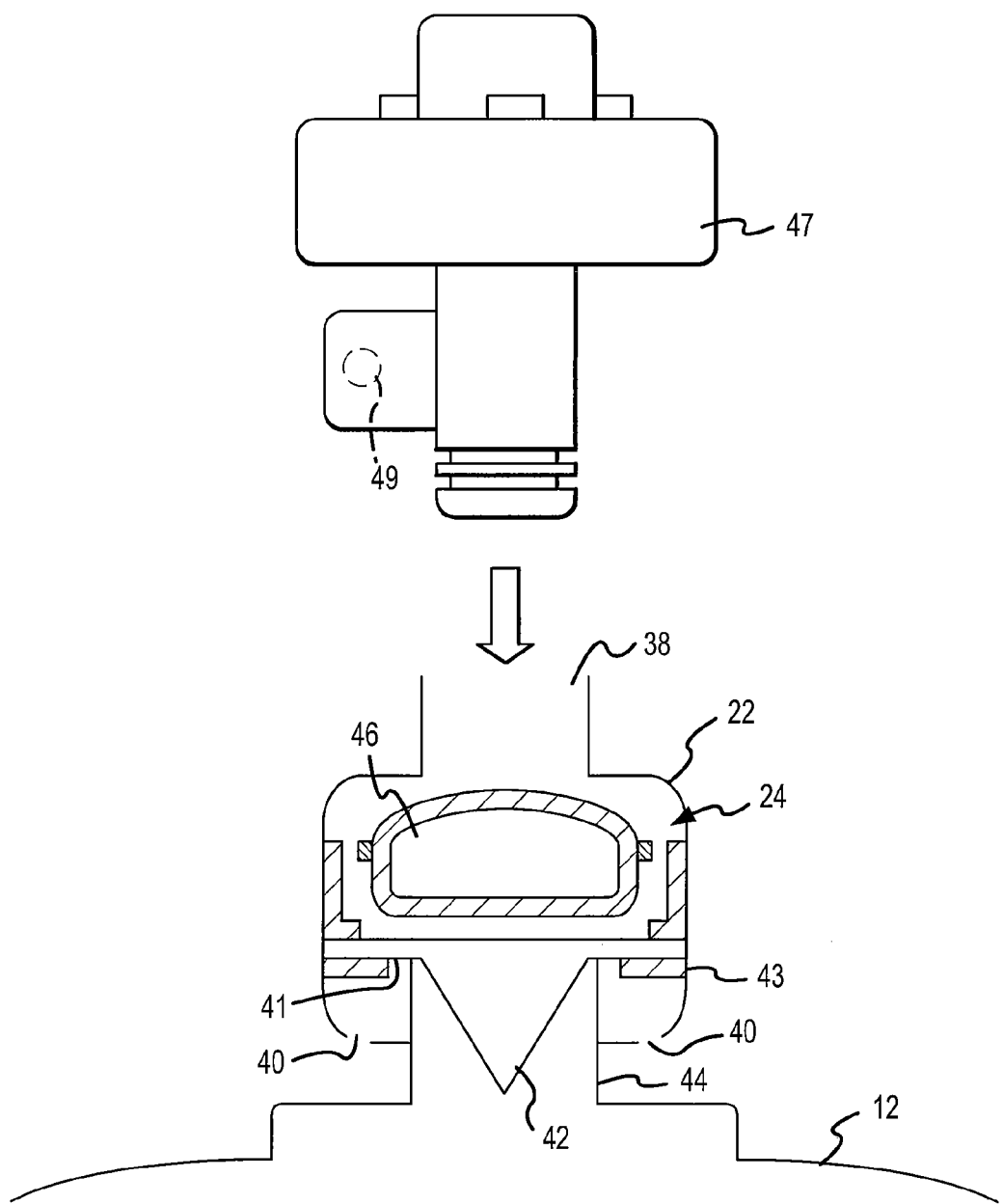
FIG. 5 illustrates the mask of FIG. 3 when coupled to an inspiratory threshold valve.

As illustrated in FIG. 5, an impedance threshold valve 47 may be coupled to port 38 to prevent respiratory gases from being drawn through valve system 24 until a threshold negative intrathoracic pressure is met or exceeded when performing chest decompressions as described in U.S. Pat. Nos. 5,551,420 and 5,692,498. When gases are forced into valve 47 (such as during a ventilation), the gases flow through valve 47 and into the mask as described in U.S. Pat. Nos. 5,551,420 and 5,692,498. Conveniently, valve 47 may be integrally formed with housing 22 or may be a separate unit that may be inserted into port 38 when needed. An optional pressure sensor 49 may be located within the valve and may, in some embodiments, be coupled to a phrenic nerve stimulator to regulate the amount of negative pressure in the chest.

Figure 6:
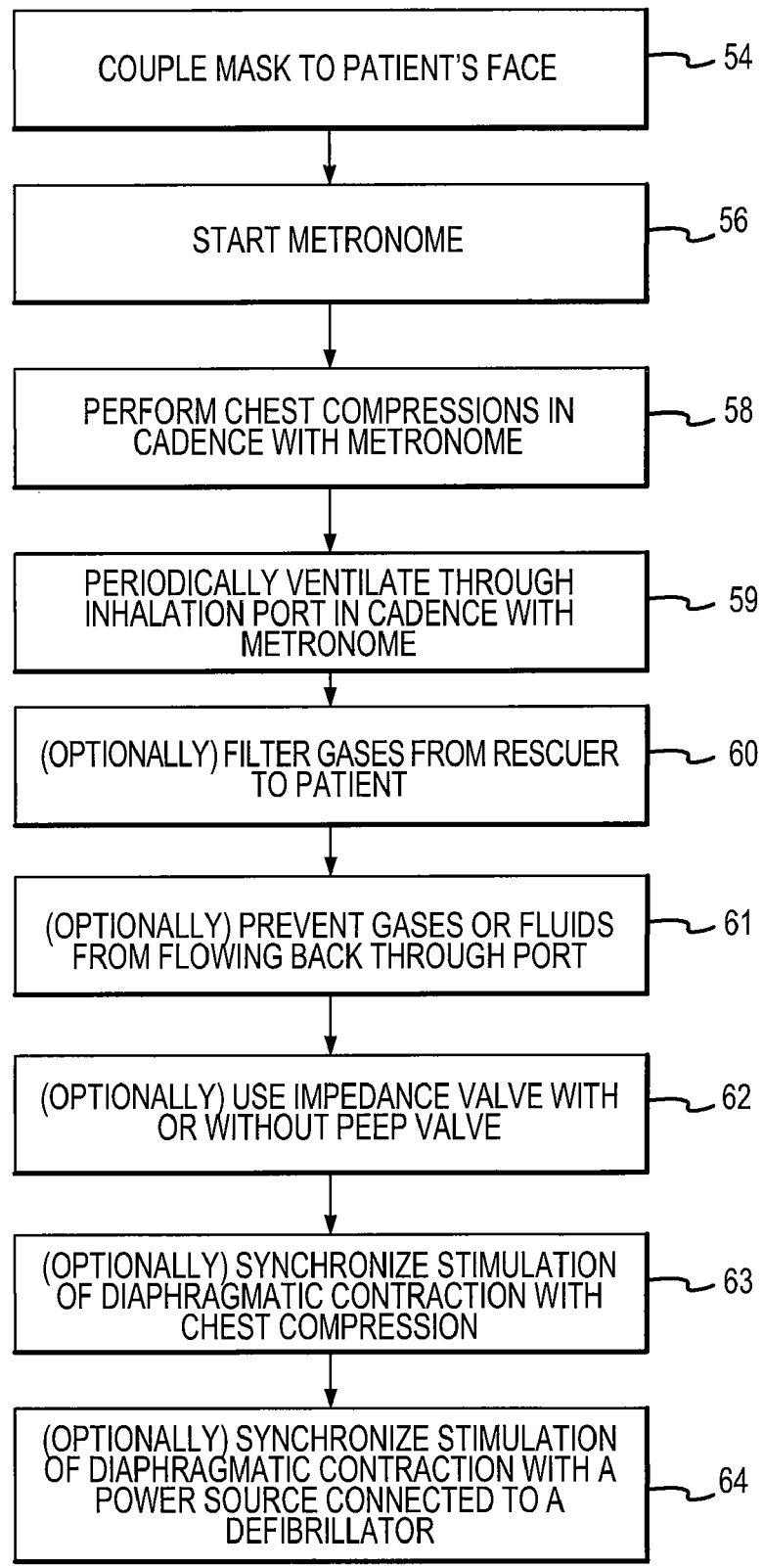
FIG. 6 is a flow chart illustrating one method for performing CPR according to the invention.

Referring now to FIG. 6, one method for performing CPR using mask 10 will be described. Initially, the mask is coupled to the patient's face as illustrated in step 54. The metronome is then turned to the "on" position as shown in step 56. With the metronome actuated, chest compressions are performed in cadence with the metronome as illustrated in step 58. Periodically, the patient is ventilated through the inhalation port in cadence with the metronome as illustrated in step 59. As previously described, an inhalation signal may periodically be produced by the metronome to indicate when ventilations should be performed. Optionally, gases from the rescuer to the patient may be filtered as illustrated in step 60.

As another optional step, gasses or fluids may be prevented from flowing back through the inhalation port and to the rescuer as shown in step 61. In another optional step, an impedance threshold valve may be used to prevent the flow of gases to the patient's lungs during the decompression phase of CPR until a threshold negative intrathoracic pressure has been met or exceeded as shown in step 62. Also, a PEEP valve may be used to prevent gases from escaping from the lungs until a certain intrathoracic pressure has been exceeded during the compression phase of CPR. As shown in step 63, the stimulation of diaphragmatic contraction may optionally be synchronized with chest compression as described in greater detail hereinafter. As shown in step 64 a power source that is connected to a defibrillator may be employed to stimulate diaphragmatic contraction. A closed loop feedback may optionally be included between a safety check valve pressure sensor and a voltage regulator to regulate the amount of intrathoracic pressure which develops with each phrenic nerve stimulation.

Figure 7:
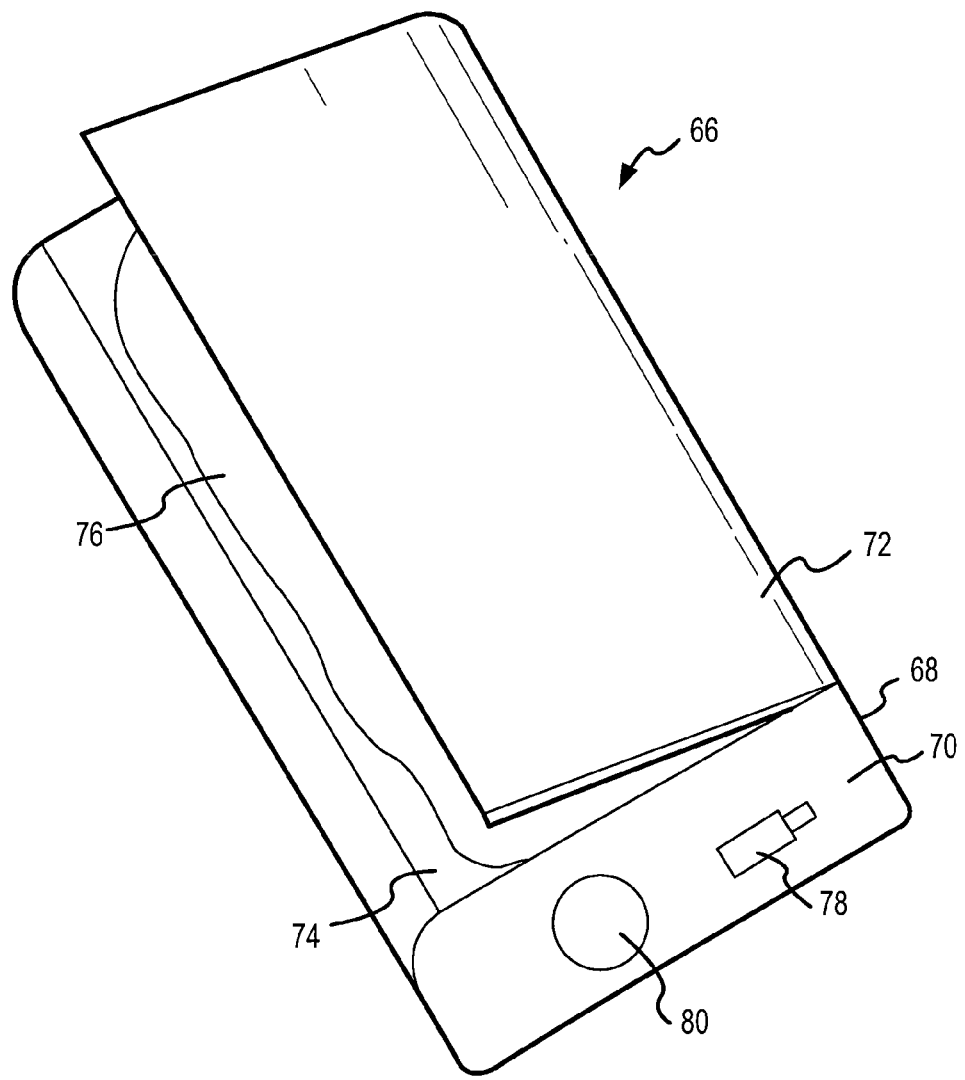
FIG. 7 is a top perspective view of a kit that may be used when performing CPR.

Referring now to FIG. 7, one embodiment of a kit 66 that may be used to facilitate the performance of CPR will be described. Kit 66 comprises a carrying case 68 having a main body 70 and a lid 72 that may be opened to gain access to a compartment 74. In this way, a facial mask 76 may be stored within compartment 74. Case 68 further includes a metronome that may be constructed in a manner similar to that previously described herein. Conveniently, an on/off slide switch 78 may be employed to turn the metronome on and off. A speaker 80 is provided to produce a repeating signal to indicate when chest compressions or ventilations are to be performed. Although not shown, it will be appreciated that one or more lights may be included on case 68 to provide a visual signal to indicate when chest compressions or ventilations are to be performed in a manner similar to that previously described.

By providing the metronome as part of carrying case 68, mask 76 may be constructed to be conventional in nature and will not need a metronome as with other embodiments. Hence, to perform CPR, lid 72 is opened and facial mask 76 is removed from compartment 74. Mask 76 is then attached to the patient's face and used to facilitate ventilation of the patient. Switch 78 may then be turned to the "on" position to produce a repeating signal to indicate when chest compressions and ventilations are to be performed.

Although not shown, a variety of attachment mechanisms may be employed to attach case 68 to a rescuer. For example, case 68 may include a clip to permit case 68 to be attached to a rescuers belt or pocket. Alternatively, one or more straps may be provided to strap case 68 about a rescuer's arm, waist, leg or the like. In this way, kit 66 is portable and may conveniently be taken to a scene where a patient needs treatment. Optionally, kit 66 may also include an impedance threshold valve, a mouthpiece that may be attached to the inhalation port, and/or a $CO_2$ sensor or sensor port to provide the rescuer with feedback from the expiratory port about the level of end tidal $CO_2$ in a manner similar to that described in connection with FIG. 8.

Figure 8:
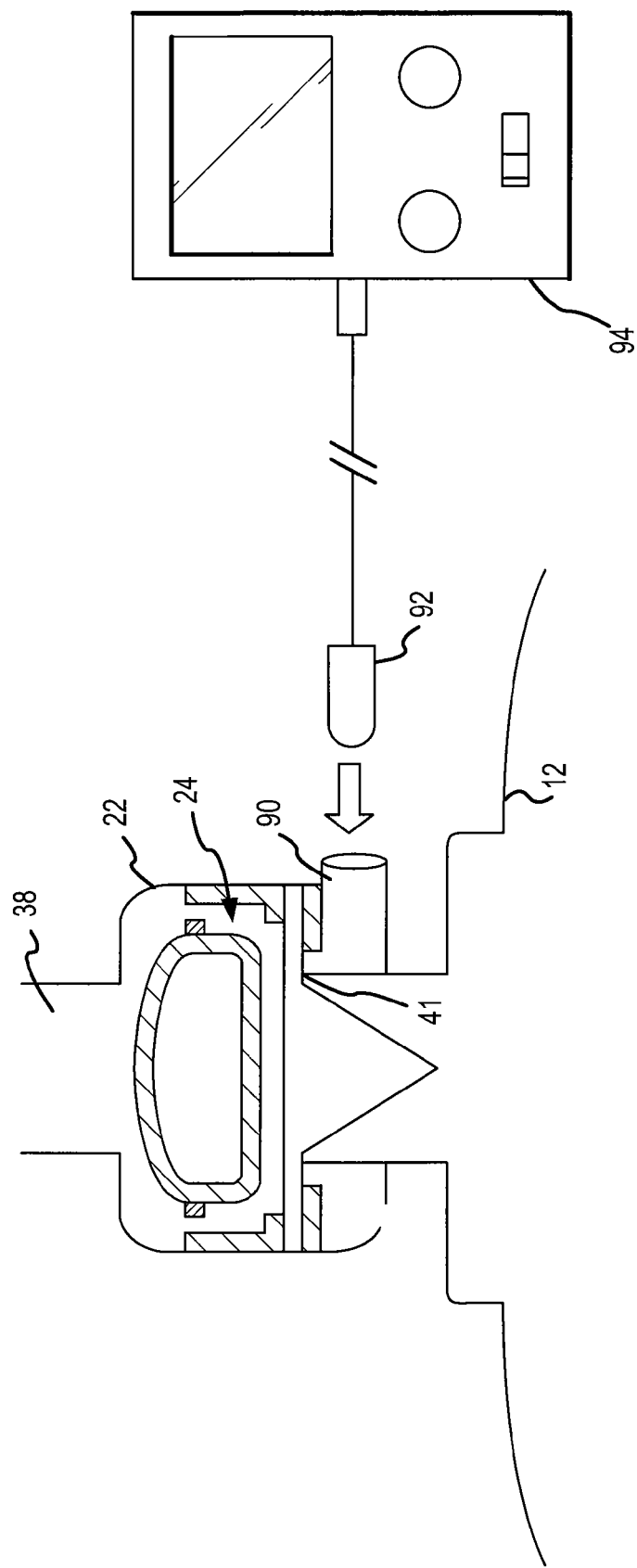
FIG. 8 illustrates the mask of FIG. 3 when used with a gas sensor system.

As shown in FIG. 8, mask 10 may optionally include an end tidal $CO_2$ sensor port 90. In this way, an end tidal $CO_2$ sensor 92 may optionally be coupled to port 90 to provide the rescuer with feedback related to the amount of $CO_2$ in expiratory gases, which is in indirect measure of the patient's cardio pulmonary circulation. Conveniently, a remote display unit 94 may be provided to display the amount of $CO_2$ measured by sensor 92.

Figure 9:
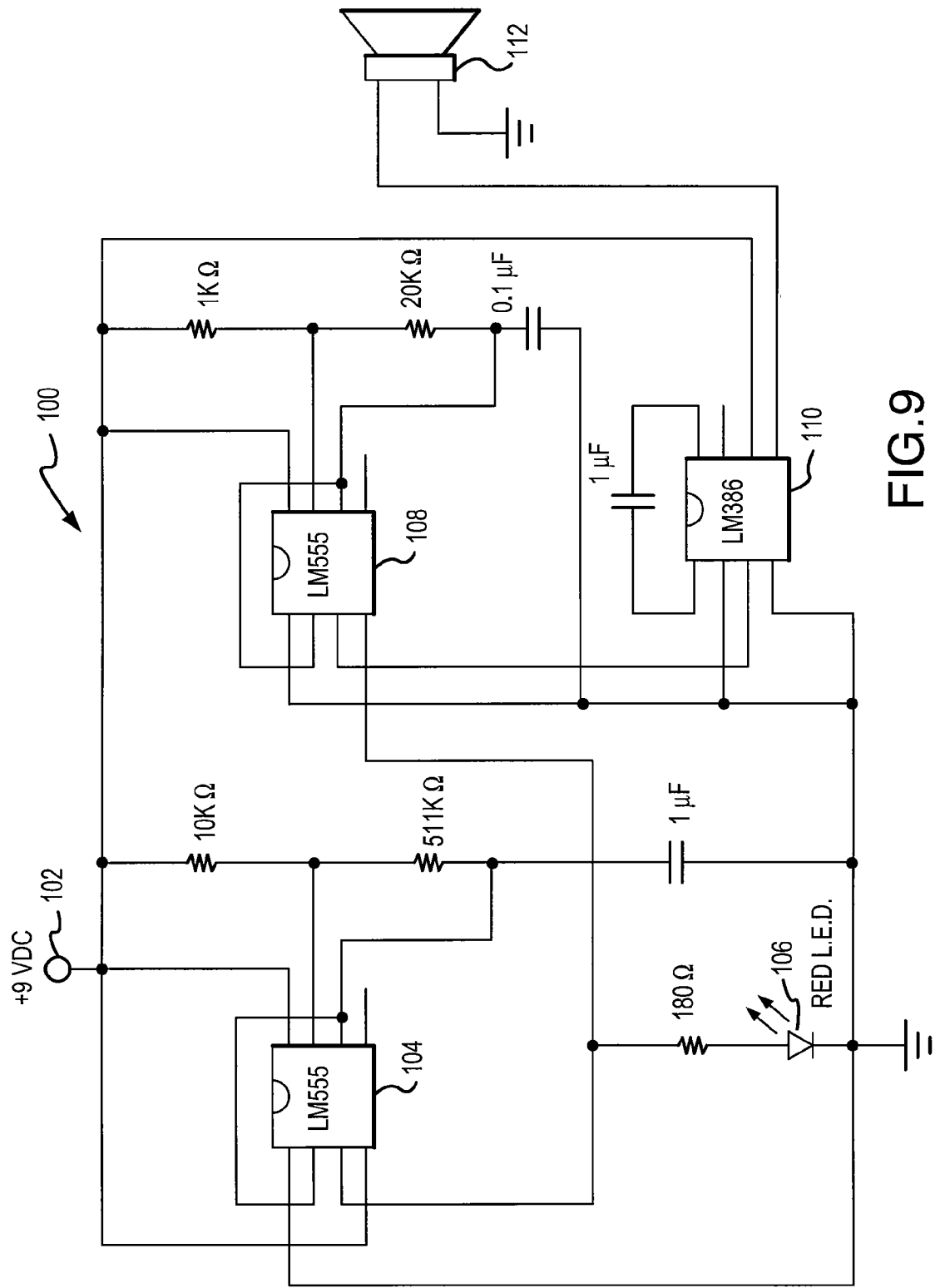
FIG. 9 illustrates an electronic circuit that may be used to generate an audible tone and a flashing visual display.

Referring now to FIG. 9, one embodiment of a circuit 100 that may be used to generate an audible tone and flashing visual display that beeps/flashes at a frequency of 1.33 to 1.66 Hz (80 to 100 beats/pulses per minute will be described). Circuit 100 is powered by a battery source 102 that supplies current to each of the individual circuit stages. A first LM555 timer 104 is configured to oscillate in the astable configuration at the previously mentioned frequency range upon power up. Each frequency output pulse has a pulse width of 750 milliseconds that illuminates a red light emitting diode 106 and triggers a second LM555 timer 108 to oscillate in the astable configuration at 351 Hz. The 351 Hz analog signal is connected to the input stage of an LM386 audio amplifier 110 which amplifies the signal and feeds it to a micro audio transducer 112 that produces an audible tone. Both the visual flash and audible tone occur simultaneously at a frequency of 1.33 to 1.66 Hz until circuit power is turned off.

Figure 10:
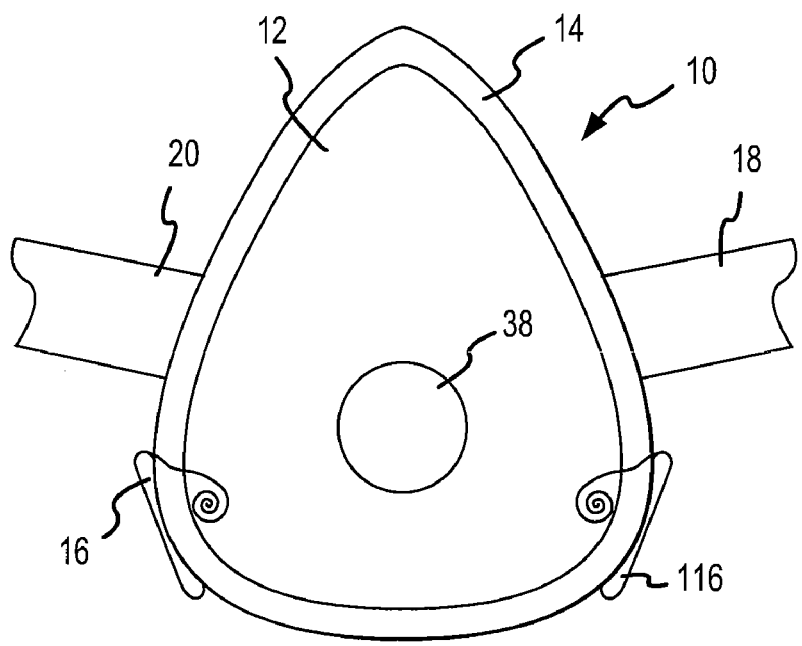
FIG. 10 illustrates a bottom view of the mask of FIG. 1 with a set of stimulating electrodes.
Figure 11:
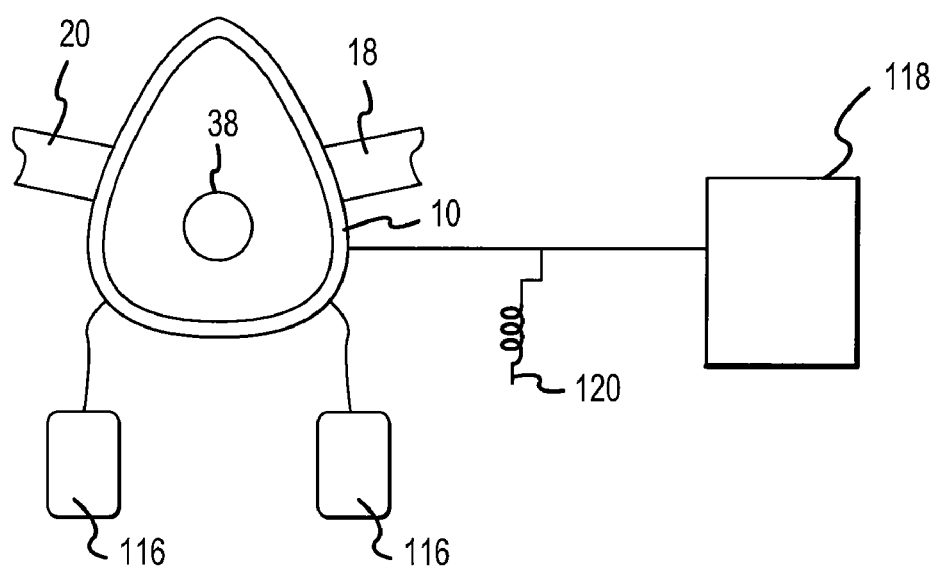
FIG. 11 illustrates the mask of FIG. 10 with a power source that may be coupled to a defibrillator to stimulate diaphragmatic contracts.

FIG. 10 illustrates a bottom view of mask 10. Optionally coupled to mask 10 are a pair of stimulation electrodes 116. As shown, electrodes 116 are coiled into a storage position. When ready for use, electrodes 116 are uncoiled as shown in FIG. 11. In use, electrodes 116 may be placed onto the patient at a location selected to stimulate the phrenic nerve to cause diaphragmatic stimulation in a manner similar to that described in copending U.S. patent application Ser. No. 09/533,880, now U.S. Pat No. 6,463,327, filed on the same date as the present application, the complete disclosure of which is herein incorporated by reference. In one embodiment, a pressure sensor, such as a pressure transducer, may be incorporated into the face mask or the impedance valve to provide feedback to a voltage regulator to maintain tracheal pressures at a given pressure during phrenic nerve stimulation. Exemplary stimulation sites for electrodes 116 are over the anterior and posterior neck regions over C3–C5 of the cervical spine. A remote power source 118 may be included to supply power to electrodes 116 when stimulation is required.

Optionally, a defibrillator connector 120 may be used to couple a defibrillator to the system to control electrical stimulation of electrodes 116. The metronome of mask 10 may optionally be electrically coupled to the defibrillator so that manual chest stimulation and phrenic nerve stimulation may be synchronously performed. In this way, a signal may be provided to the rescuer indicating when chest compressions should occur which will be at the same time that phrenic nerve stimulation occurs to cause the diaphragm to contract.

As another alternative, mask 10 with electrodes 116 may be included as part of a kit in a manner similar to that previously described in connection with FIG. 7. With this alternative, the carrying case may include a power supply and circuitry to supply current to electrodes 116. The carrying case may also contain controls to regulate the flow of current to the electrodes, the timing of pulsation, the pulse width, and the like.

The invention has now been described in detail for purposes of clarity and understanding. However, it will be appreciated that certain changes and modifications may be practiced within the scope of the appended claims.

What is claimed is:

1. A rescue system comprising:
   a pressure-responsive valve system to permit the inflow of respiratory gases into a patient's lungs and to permit the outflow of respiratory gases from the patient's lungs, wherein the valve system is configured to prevent the inflow of respiratory gases into the patient's lungs until a certain negative intrathoracic pressure has been achieved, whereupon the valve system operates to allow gases to flow into the patient's lungs;
   a metronome operably coupled to the valve system to produce a repeating chest compression signal to facilitate the performance of regular chest compressions or breathing when performing cardiopulmonary resuscitation;
   a mask body that is adapted to be coupled to a patient's face; and
   one or more stimulation electrodes operably coupled to the mask body.

2. A system as in claim 1, wherein the metronome is configured to produce the repeating chest compression signal a constant rate in the range from about 50 signals per minute to about 100 signals per minute.

3. A system as in claim 1, wherein the metronome includes at least one light source that is repeatedly lighted to produce the repeating signal.

4. A system as in claim 1, wherein the metronome includes at least one speaker to repeatedly produce an audible signal or verbal command.

5. A system as in claim 1, wherein the metronome is further configured to produce a repeating audible ventilation signal to facilitate the performance of regular ventilations when performing cardiopulmonary resuscitation.

6. A system as in claim 5, wherein the metronome is configured to produce the repeating audible ventilation signal one to two times about every 5 to about 25 chest compression signals.

7. A system as in claim 1, wherein the valve system includes an inhalation port and an exhalation port, wherein the valve system is configured such that respiratory gases are permitted to flow through the inhalation port when respiratory gases are introduced into the mask through the inhalation port, and such that expired gases are prevented from passing through the inhalation port while being permitted to flow out of the exhalation port when respiratory gases are expired by the patient into the mask.

8. A system as in claim 7, wherein the valve system further comprises a fish mouth membrane valve unit that is configured to block gas flow to the exhalation port when gases are introduced into the inhalation port, and to permit gases exhaled by the patient to flow to the exhalation port while preventing the gases from flowing to the inhalation port.

9. A system as in claim 1, further comprising an inflatable bladder coupled to a bottom end of the mask body, and at least one head strap coupled to the mask body that is adapted to secure the mask to the patient's face.

10. A system as in claim 1, further comprising an adhesive coupled to a bottom end of the mask body to assist in securing the mask to the patient's face.

11. A system as in claim 1, further comprising a power supply to provide powder to the metronome, and wherein the power supply and metronome are disposed in a replaceable module that is removably coupled to the mask body.

12. A system as in claim 1, wherein the valve system further comprises a expiration valve that prevent gases from exiting the mask body until a threshold positive pressure is produced within the mask body.

13. A system as in claim 1, further comprising an inflatable bladder coupled to a bottom end of the mask body, and at least one head strap coupled to the mask body that is adapted to secure the mask to the patient's face.

14. A system as in claim 1, further comprising an adhesive coupled to a bottom end of the mask body to assist in securing the mask to the patient's face.

15. A system as in claim 1, further comprising a power supply to provide powder to the metronome, and wherein the power supply and metronome are disposed in a replaceable module that is removably coupled to the mask body.

16. A rescue system comprising:
a valve system to regulate the inflow of respiratory gases into a patient's lungs and to permit the outflow of respiratory gases from the patient's lungs, the valve system further including a threshold valve that prevents respiratory gases flow flowing into the mask body until a threshold negative pressure is met or exceeded;
a metronome operably coupled to the valve system to produce a repeating chest compression signal to facilitate the performance of regular chest compressions or breathing when performing cardiopulmonary resuscitation;
a mask body that is coupled to the valve system, wherein the mask body is adapted to be coupled to a face of the patient; and
one or more stimulation electrodes operably coupled to the mask body, and a power source to supply electrical current to the electrodes.

17. A system as in claim 16, wherein the metronome is configured to produce the repeating chest compression signal a constant rate in the range from about 50 signals per minute to about 100 signals per minute.

18. A system as in claim 16, wherein the metronome includes at least one light source that is repeatedly lighted to produce the repeating signal.

19. A system as in claim 16, wherein the metronome includes at least one speaker to repeatedly produce an audible signal or verbal command.

20. A system as in claim 16, wherein the metronome is further configured to produce a repeating audible ventilation signal to facilitate the performance of regular ventilations when performing cardiopulmonary resuscitation.

21. A system as in claim 20, wherein the metronome is configured to produce the repeating audible ventilation signal one to two times about every 5 to about 25 chest compression signals.

22. A system as in claim 16, wherein the valve system further includes an inhalation port and an exhalation port, wherein the valve system is configured such that respiratory gases are permitted to flow through the inhalation port when respiratory gases are introduced into the mask through the inhalation port, and such that expired gases are prevented from passing through the inhalation port while being permitted to flow out of the exhalation port when respiratory gases are expired by the patient into the mask.

23. A system as in claim 22, wherein the valve system further comprises a fish mouth membrane valve unit that is configured to block gas flow to the exhalation port when gases are introduced into the inhalation port, and to permit gases to flow to the exhalation port while preventing the gases from flowing to the inhalation port when gases are expired by the patient into the mask.

24. A system as in claim 22, one or more sensors coupled to the inhalation port and/or the exhalation port to measure certain gas exchange parameters.

25. A method for performing cardio pulmonary resuscitation, the method comprising:
interfacing a rescue system with a patient's airway, wherein the rescue system includes a metronome that is operably coupled to a valve system to permit the inflow of respiratory gases into the patient's lungs and to permit the outflow of respiratory gases from the patient's lungs;
preventing with the valve system respiratory gases flow flowing into the lungs until a threshold negative pressure is met or exceeded;
actuating the metronome to produce a repeating signal;
performing chest compressions in cadence with the repeating signal;
electrically stimulating the patient with one or more electrodes that are coupled to the rescue system.

26. A method as in claim 25, further comprising producing the repeating signal a constant rate in the range from about 50 signals per minute to about 100 signals per minute.

27. A method as in claim 25, further comprising producing with the metronome a repeating visual signal.

28. A method as in claim 25, further comprising producing with the metronome a repeating audible signal.

29. A method as in claim 25, further comprising periodically supplying a respiratory gas to the patient through the valve system.

30. A method as in claim 29, wherein the valve system includes an inhalation port for supplying respiratory gases to the patient, and further comprising preventing with the valve system any expired respiratory gases from the patient from passing through the inhalation port.

31. A method as in claim 30, wherein the gas supplying step comprises blowing into the inhalation port or squeezing a ventilatory bag that is coupled to the inhalation port.

32. A method as in claim 25, further comprising preventing expired respiratory gases from exiting the lungs until a certain pressure within the lungs is met or exceeded.

33. A method as in claim 25, wherein the rescue system includes a mask, and further comprising coupling the mask to the patient's face with a strap that is placed about the patient's head.

34. A method as in claim 25, wherein the rescue system includes a mask, and further comprising coupling the mask to the patient's face with an adhesive that is coupled to the mask.

* * * * *